United States Patent
Li et al.

(12) 
(10) Patent No.: US 12,343,411 B2
(45) Date of Patent: Jul. 1, 2025

(54) COMPOSITIONS AND METHODS FOR TREATING KERATINOUS SUBSTRATES

(71) Applicant: L'Oreal, Paris (FR)

(72) Inventors: Dongcui Li, Metuchen, NJ (US); Heather Lee, Wayne, NJ (US); Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 793 days.

(21) Appl. No.: 15/931,270

(22) Filed: May 13, 2020

(65) Prior Publication Data

US 2020/0375854 A1    Dec. 3, 2020

Related U.S. Application Data

(60) Provisional application No. 62/855,415, filed on May 31, 2019.

(51) Int. Cl.
| | | |
|---|---|---|
| A61K 8/04 | (2006.01) | |
| A61K 8/34 | (2006.01) | |
| A61K 8/365 | (2006.01) | |
| A61K 8/37 | (2006.01) | |
| A61K 8/42 | (2006.01) | |

(Continued)

(52) U.S. Cl.
CPC ............ *A61K 8/042* (2013.01); *A61K 8/342* (2013.01); *A61K 8/345* (2013.01); *A61K 8/365* (2013.01); *A61K 8/375* (2013.01); *A61K 8/42* (2013.01); *A61K 8/922* (2013.01); *A61Q 5/06* (2013.01); *A61K 2800/48* (2013.01)

(58) Field of Classification Search
CPC ........ A61K 8/042; A61K 8/365; A61K 8/342; A61K 8/0295; A61K 8/44; A61K 8/375; A61Q 5/002
See application file for complete search history.

(56) References Cited

U.S. PATENT DOCUMENTS

| | | |
|---|---|---|
| 5,429,815 A | 7/1995 | Faryniarz et al. |
| 6,379,681 B1 | 4/2002 | Bordat et al. |

(Continued)

FOREIGN PATENT DOCUMENTS

| | | |
|---|---|---|
| CA | 2087691 A1 | 7/1993 |
| DE | 197 13 793 A1 | 10/1998 |

(Continued)

OTHER PUBLICATIONS

International Search Report and Written Opinion for counterpart Application No. PCT/US2020/033099, mailed Jul. 23, 2020.

*Primary Examiner* — Timothy P Thomas
(74) *Attorney, Agent, or Firm* — The Marbury Law Group, PLLC

(57) ABSTRACT

Disclosed are semi-solid gel compositions comprising (a) a gelling oil phase comprising: i) at least one oil gelator; ii) at least one fatty alcohol; and iii) at least one fatty compound other than (ii); wherein said gelling oil phase is present in an amount of from at least about 50% by weight, relative to the weight of the total composition; and (b) a lamellar crystalline aqueous gel phase comprising: i) water and optionally at least one polyol present in an amount up to about 50% by weight, relative to the weight of the total composition; ii) at least one lamellar crystalline phase structurant; and iii) at least one emulsifier. The disclosure also relates to methods of treating keratinous substrates.

20 Claims, 6 Drawing Sheets

Apply the product

Scrubbing for 3 sec

(51) Int. Cl.
  *A61K 8/92* (2006.01)
  *A61Q 5/06* (2006.01)

(56) References Cited

U.S. PATENT DOCUMENTS

| | | |
|---|---|---|
| 2006/0024256 A1 | 2/2006 | Wells et al. |
| 2014/0162979 A1 | 6/2014 | Palla-Venkata et al. |
| 2018/0303727 A1 | 10/2018 | Riedel et al. |

FOREIGN PATENT DOCUMENTS

| | | | | |
|---|---|---|---|---|
| EP | 0 556 957 A1 | | 8/1993 | |
| EP | 2062563 A1 | | 5/2009 | |
| EP | 2638921 A1 | * | 9/2013 | ........... A61K 8/0216 |
| EP | 3165216 A1 | | 5/2017 | |

* cited by examiner

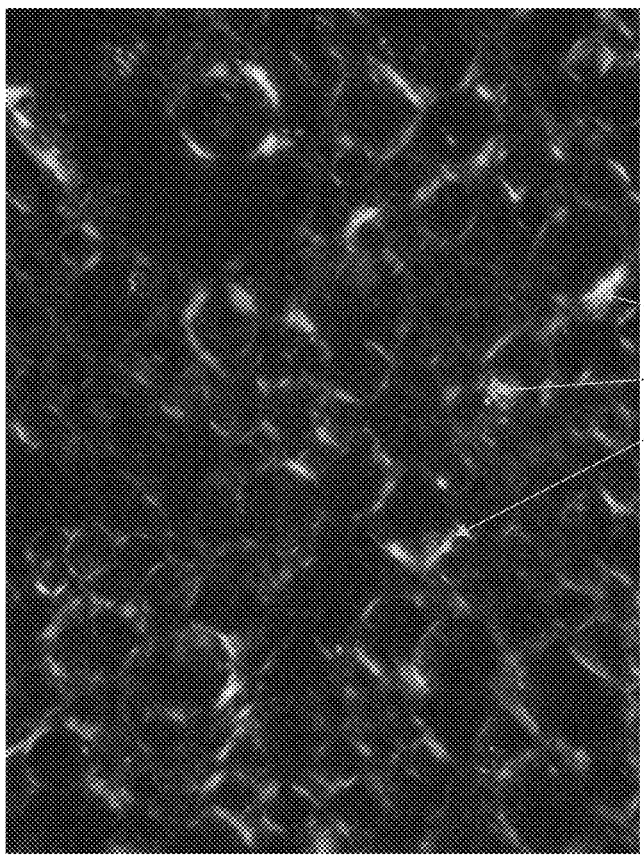
Fig. 1b — Water/Polyol lamellar crystalline gel network phase
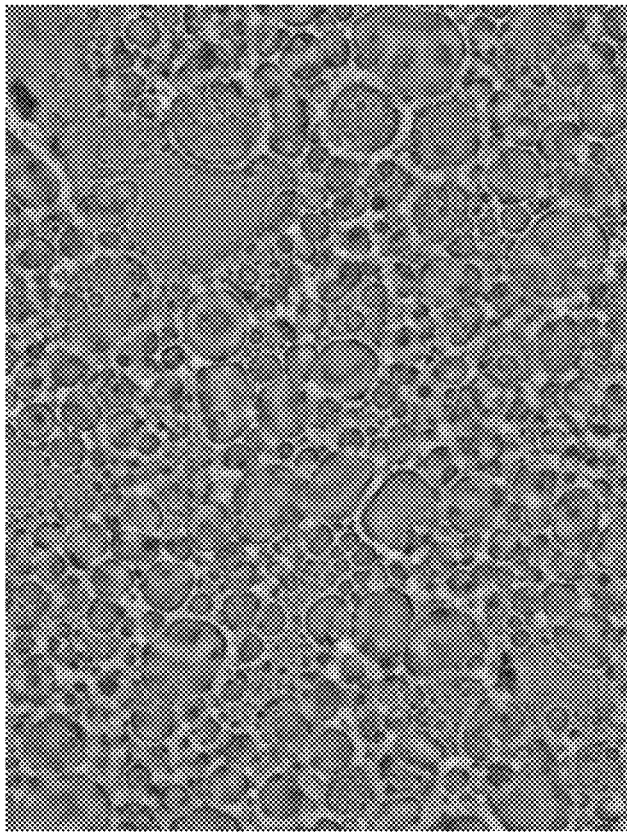
Fig. 1a — Oil phase

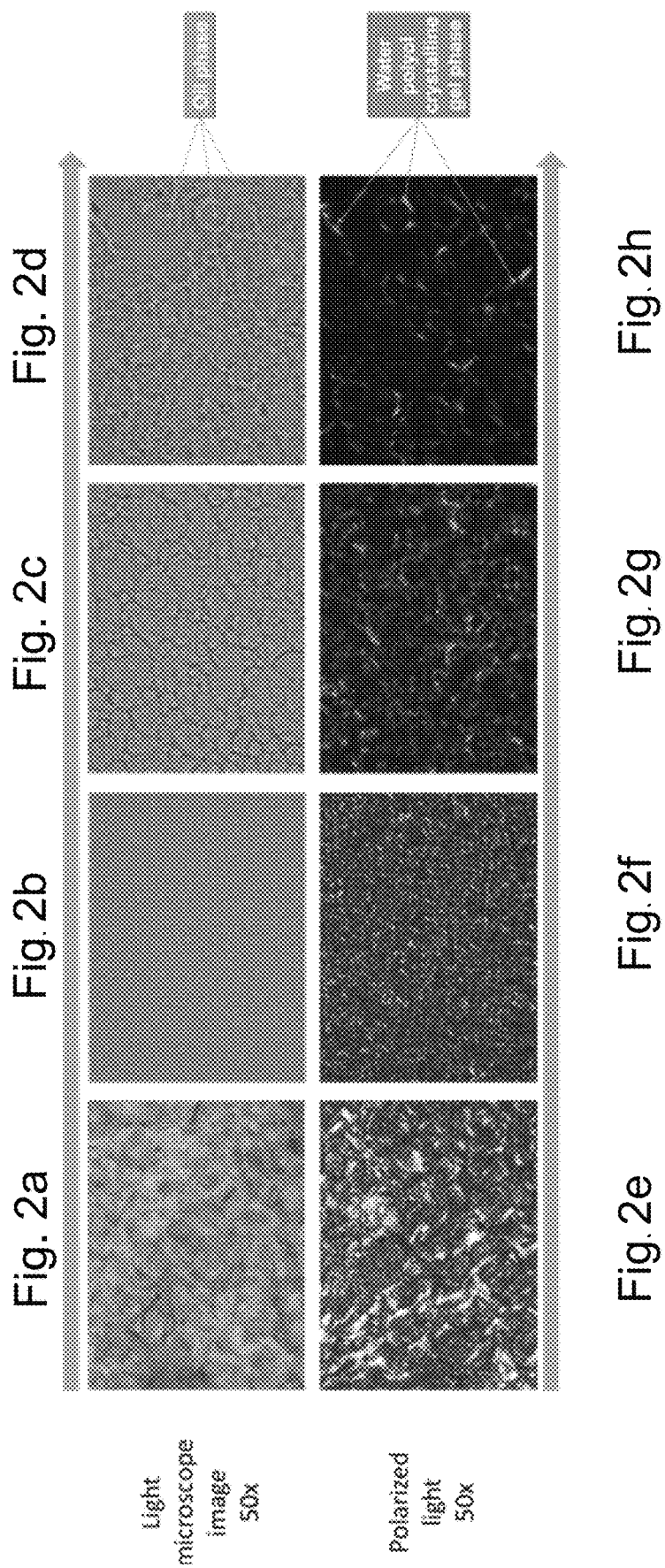

Transformation to oil

Scrubbing for 3 sec

Apply the product

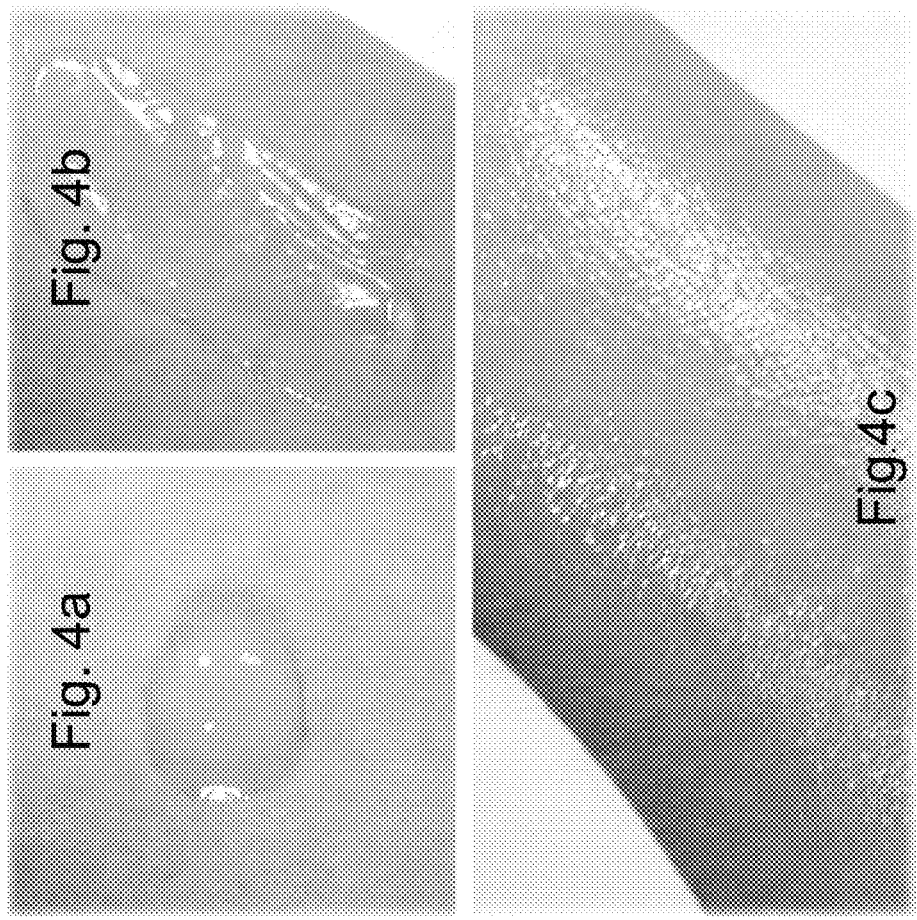

COMPOSITIONS AND METHODS FOR TREATING KERATINOUS SUBSTRATES

CROSS-REFERENCE TO RELATED APPLICATIONS

This application claims priority to U.S. Provisional Patent Application No. 62/855,415, filed May 31, 2019.

TECHNICAL FIELD

The disclosure relates to compositions and methods for treating keratinous substrates. The compositions are solid or semi-solid gel compositions comprising (a) at least one gelling oil phase and (b) at least one lamellar crystalline aqueous gel phase. The solid or semi-solid gel composition according to the disclosure can transform to a liquid gel composition upon application of shear forces.

BACKGROUND

Leave-in compositions comprising oil for treating keratinous substrates such as hair and skin are known, such as, for example, hair and body/face oils, lotions, serums, smoothing creams, etc. The goal of many of these compositions includes conditioning, smoothing, imparting shine, and to decrease or eliminate the appearance of frizz or rough patches. However, these compositions can make keratinous substrates appear excessively greasy. Consumers also find the liquid viscosity of hair and body/face oils less than desirable to manipulate and apply, whereas the creamier formulations can be sticky and may leave a residue.

Additionally, a growing number of consumers are looking for more environmentally conscious, naturally-based products, including leave-in treatments to smooth, impart shine, condition, and/or decrease or eliminate the appearance of frizz or dry patches. Consumers seek naturally-based products having a comparable degree of smoothing, imparting shine, conditioning, and/or decreasing or eliminating the appearance of frizz and rough patches as synthetic leave-in treatments. Thus, there is a need for naturally-based leave-in treatment compositions which impart these cosmetic properties.

SUMMARY

It has now been surprisingly and unexpectedly discovered that combining at least one gelling oil phase and at least one lamellar crystalline aqueous gel phase results in a leave-in treatment with a unique transformative texture that delivers shine, moisture, smoothness, natural feeling, and manageability of keratinous substrates without greasiness or residues. The solid or semi-solid gel compositions according to various embodiments of the disclosure include a lamellar crystalline oil gel which transforms to liquid oil upon application of shear. The solid or semi-solid gel can have a gel, balm, paste, or cream consistency prior to shearing. The unique microstructure and solid-to-liquid transformation properties result from a gelling oil phase that is well dispersed in a continuous lamellar crystalline aqueous gel phase. In various embodiments, the compositions and methods provide properties of nourishment, moisture, and smoothness to the keratinous substrates, while leaving a natural and clean feeling. The disclosed compositions impart to hair more moisture, more detangling, ease of blow drying, more smoothness, a more natural and "clean" feeling, and more manageability than standard leave-in oil comprising compositions. The disclosed compositions impart to ski more moisture, more smoothness, more softness, a more natural and "clean" feeling, and more manageability than standard body/face oil comprising compositions.

According to various embodiments, the solid or semi-solid gel compositions may comprise: (a) a gelling oil phase comprising: i) at least one oil gelator; ii) at least one fatty alcohol; and iii) at least one fatty compound other than (ii); wherein said gelling oil phase is present in an amount of from at least about 50% by weight, relative to the weight of the total composition; and (b) a lamellar crystalline aqueous gel phase comprising: i) water and optionally at least one polyol present in an amount up to about 50% by weight, relative to the weight of the total composition; ii) at least one lamellar crystalline phase structurant; and iii) at least one emulsifier.

Various embodiments also relate to keratinous substrate treatment compositions comprising the solid or semi-solid gels, and methods of treating the substrate with the solid or semi-solid gel compositions.

BRIEF DESCRIPTION OF THE DRAWINGS

FIG. 1a is a 50× light microscope image of a semi-solid gel according to an exemplary embodiment of the disclosure. Exemplary oil phase droplets are labeled with arrows.

FIG. 1b is a 50× polarized light microscope image of a semi-solid gel according to an exemplary embodiment of the disclosure. Exemplary lamellar crystalline gel phase structures are labeled with arrows.

FIGS. 2a-2d depict light microscope images at 50× of semi-solid gels according to an exemplary embodiment of the disclosure, wherein the concentration of water/polyol and oil gelator and the oil droplet size increases from photograph 2a to photograph 2d. The oil phase is labeled in FIG. 2d. FIGS. 2e-2h depict polarized light images at 50× of semi-solid gels according to an exemplary embodiment of the disclosure, wherein the concentration of water/polyol and oil gelator and the oil droplet size increases from photograph 2e to photograph 2h. The water/polyol crystalline gel phase is labeled in FIG. 2h.

FIG. 4a is a photograph of a sample of a semi-solid gel, according to an exemplary embodiment of the disclosure, placed on skin.

FIG. 4b is a photograph of a sample of a semi-solid gel, according to an exemplary embodiment of the disclosure, spread on skin using a hand with three swipes for approximately 3 seconds.

FIG. 4c is a photograph of a semi-solid gel, according to an exemplary embodiment of the disclosure, that has been rubbed onto skin with a hand.

DESCRIPTION OF EXEMPLARY EMBODIMENTS

Figure 3C:
FIG. 3c is a photograph of a semi-solid gel, according to an exemplary embodiment of the disclosure, that has been rubbed onto skin with a hand.
Figure 3B:
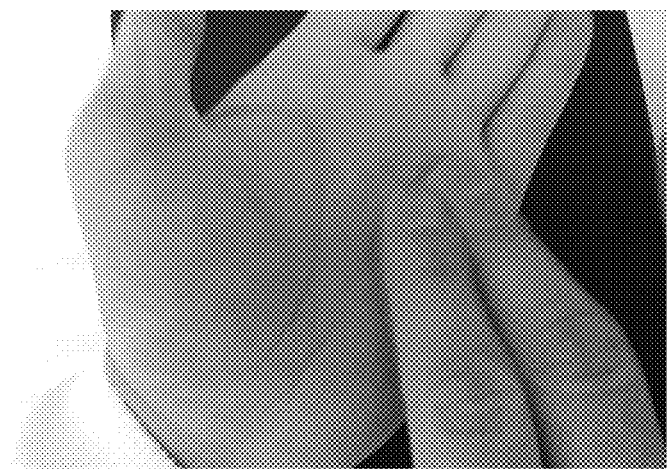
FIG. 3b is a photograph of a sample of a semi-solid gel, according to an exemplary embodiment of the disclosure, spread on skin using a hand with three swipes for approximately 3 seconds.
Figure 3A:
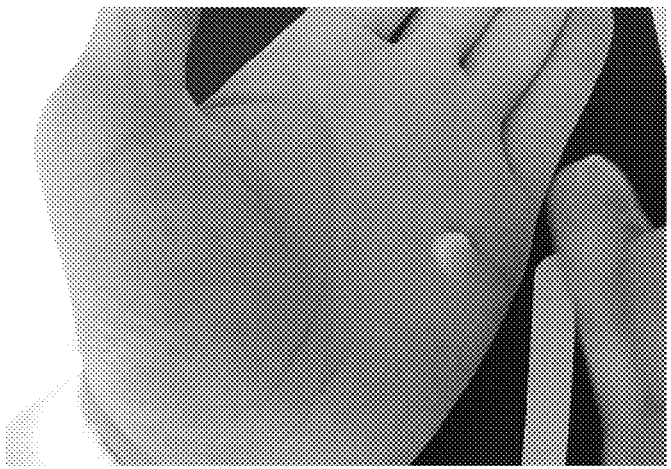
FIG. 3a is a photograph of a sample of a semi-solid gel, according to an exemplary embodiment of the disclosure, placed on skin.
Figure 5B:
FIG. 5b is a photograph of a head of dry hair treated as described in Example 3. The hair on the left-hand side of the photograph was treated with a semi-solid gel corresponding to Inventive Composition B, in Table 1 of Example 2. The hair on the right-hand side of the photograph was treated with a cream corresponding to Comparative Composition F, in Table 2 of Example 3. Hair treated with Inventive Composition B was more supple and smooth, and had less white residue, than hair treated with Comparative Composition F. In addition, the hair on the left side felt soft, moisturized hair, while the hair on the right side felt crunchy and dry.
Figure 5A:
FIG. 5a is a photograph of a head of wet hair treated as described in Example 3. The hair on the left-hand side of the photograph was treated with a semi-solid gel corresponding to Inventive Composition B, in Table 1 of Example 2. The hair on the right-hand side of the photograph was treated with a cream corresponding to Comparative Composition F, in Table 2 of Example 3. Hair treated with Inventive Composition B was more supple and smooth, and had less white residue, than hair treated with Comparative Composition F. In addition, the hair on the left side felt like baby soft, moisturized hair, while the hair on the right side felt crunchy.
Figure 6:
FIG. 6 is a photograph of a head of wet hair treated as described in Example 4. The hair on the left-hand side of the photograph was treated with a semi-solid gel corresponding to Inventive Composition A, in Table 1 of Example 2. The hair on the right-hand side of the photograph was treated with an oil corresponding to Comparative Composition G, in Table 3 of Example 4. Inventive Composition A and Comparative Composition G imparted comparable cosmetic properties on the hair.

The disclosure relates, in various embodiments, to solid or semi-solid gel compositions which may comprise: (a) a gelling oil phase comprising: i) at least one oil gelator; ii) at least one fatty alcohol; iii) at least one fatty compound other than (ii); wherein said gelling oil phase is present in an amount of from at least about 50% by weight, relative to the weight of the total composition; and (b) a lamellar crystalline aqueous gel phase comprising: i) water and optionally at least one polyol present in an amount up to about 50% by weight, relative to the weight of the total composition; ii) at least one lamellar crystalline phase structurant; and iii) at least one emulsifier.

Accordingly, to various embodiments, the semi-solid gel is a lamellar crystal semi-solid oil gel. According to at least certain exemplary embodiments, the lamellar crystal semi-solid gel is stable.

In an embodiment, the disclosure relates to semi-solid gel compositions comprising: (a) a gelling oil phase comprising: i) at least one oil gelator; ii) at least one fatty alcohol; iii) at least one fatty compound other than (ii); wherein said gelling oil phase is present in an amount of from at least about 50% by weight, relative to the weight of the total composition; and (b) a lamellar crystalline aqueous gel phase comprising: i) water and optionally at least one polyol present in an amount up to about 50% by weight, relative to the weight of the total composition; ii) at least one lamellar crystalline phase structurant; and iii) at least one emulsifier.

A "gel" as used herein means a structure containing a fluid within a three-dimensional network structure, such as an emulsion, resulting in a semi-solid composition. A gel is formed using a substance with a gel-forming ability, referred to as a "gelator." When the fluid is an organic liquid other than water (such as an organic solvent or an oil), the gel is referred to as an "organogel" or an "oil gel." The term "oil gelator" means a substance that can gel an oil to form an oil gel. The disclosed gels can be in a solid or semi-solid state. The terms "solid" and "semi-solid" can be used interchangibly and include liquid compositions.

According to various embodiments, the weight ratio of (a) the gelling oil phase to (b) the lamellar crystalline gel phase, as active material, ranges from about 5:1 to about 1:1, of gelling oil phase:lamellar crystalline gel phase, such as from about 4:1 to about 1:1, about 3:1 to about 1:1, about 2:1 to about 1:1, or about 3:2.

Gelling Oil Phase

According to various exemplary embodiments of the disclosure, the semi-solid gel composition comprises (a) a gelling oil phase. According to various exemplary embodiments, the gelling oil phase may comprise: i) at least one oil gelator; ii) at least one fatty alcohol; iii) at least one fatty compound other than (ii); wherein said gelling oil phase is present in an amount of from at least about 50% by weight, relative to the weight of the total composition.

The gelling oil phase (a) may, according to various embodiments, be present in the semi-solid gel in an amount ranging from at least about 50% by weight of the total composition, such as, for example, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, or at least about 70%. By way of non-limiting example, the gelling oil phase (a) may be present in the composition in an amount ranging from about 50% to about 70%, about 50% to about 69%, about 50% to about 68%, about 50% to about 67%, about 50% to about 66%, about 50% to about 65%, about 50% to about 64%, about 50% to about 63%, about 50% to about 62%, about 50% to about 61%, about 50% to about 60%, about 51% to about 64%, about 51% to about 63%, or about 51% to about 62%, by weight of the total composition.

Oil Gelators

As described herein, the gelling oil phase present according to various embodiments comprises one or more oil gelators. The oil gelators present according to various embodiments include gelators that can solidify or gelatinize oily components such as fats, oils, waxes, hydrocarbon oils, higher fatty acids, higher alcohols, ester oils, silicon oils, or a mixture thereof. The oil gelators of the present invention may also be called gelling agents and may be used as thickening agents.

The oil gelators of the present invention can include esters and/or amides of fatty acid gellants, hydroxy acids, hydroxy fatty acids, cholesterolic materials, lanolinolic materials, other amide gellants, or crystalline gellants.

Amide gellants including N-acyl amino acid amides useful herein are prepared from glutamic acid, lysine, glutamine, aspartic acid or mixtures thereof. Particularly preferred are n-acyl glutamic acid amides corresponding to the following formula: [060"] R—NH—CO—(CH2)2-CH—(NH—CO—R)—CO—NH—R wherein R is an aliphatic hydrocarbon radical having from about 12 to about 22 carbon atoms, and R is an aliphatic hydrocarbon radical having from about 4 to about 12 carbon atoms. Non-limiting examples of these include n-lauroyl-L-glutamic acid dibutyl amide, n-stearoyl-L-glutamic acid diheptyl amide, or mixtures thereof. Most preferred is n-lauroyl-L-glutamic acid dibutyl amide, also referred to as dibutyl lauroyl glutamide, is used. This material is commercially available under the tradename Gelling agent GP-1 available from Ajinomoto.

Other gelling agents suitable for use in the compositions include 12-hydroxystearic acid and/or salts thereof, esters of 12-hydroxystearic acid, amides of 12-hydroxystearic acid or combinations thereof. These preferred gellants include those which correspond to the following formula:

R—CO—(CH2)10-(CH—(OH)—(CH2)5-CH3 wherein R is R or NRR; and R and R are hydrogen, or an alkyl, aryl, or arylalkyl radical which is branched linear or cyclic and has from about 1 to about 22 carbon atoms; preferably, from about 1 to about 18 carbon atoms. R and R may be either the same or different. In an embodiment, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, or mixtures thereof; even more preferably, 12-hydroxystearic acid, isopropyl amide of 12-hydroxystearic acid, or combinations thereof. Most preferred is 12-hydroxystearic acid.

Suitable amide gellants include disubstituted or branched monoamide gellants, monosubstituted or branched diamide gellants, triamide gellants, or combinations thereof, excluding the n-acyl amino acid derivatives selected from the group consisting of n-acyl amino acid amides, n-acyl amino acid esters prepared from glutamic acid, lysine, glutamine, apartic acid, or combinations thereof, several of which are specifically disclosed in U.S. Pat. No. 5,429,816.

Alkyl amides or di- or tri-basic carboxylic acids or anhydrides suitable for use in the composition include alkyl amides of citric acid, tricarballylic acid, aconitic acid, nitrilotriacetic acid, succinic acid or itaconic acid such as 1,2,3-propane tributylamide, 2-hydroxy-1,2,3-propane tributylam ide, 1-propene-1,2,3-triotylamide, N,N',N''-tri (acetodecylamide)amine, 2-dodecyl-N,N'-dihexylsuccinamide, or 2 dodecyl-N,N'-dibutylsuccinamide. Preferred are alkyl amides of di-carboxylic acids such as di-amides of alkyl succinic acids, alkenyl succinic acids, alkyl succinic anhydrides or alkenyl succinic anhydrides, more preferably 2-dodecyl-N,N'-dibutylsuccinamide.

Preferred solid non-polymeric gellants for use herein include those enantomeric compounds or materials containing at least one asymmetric (chiral) carbon atom. Non-limiting examples of these preferred enantomeric gellants include 1 2-hydroxystearic acid, other hydroxy acids such as alpha hydroxy acids, cholesterols, lanolin, or derivatives thereof.

By way of non-limiting example only, 12-hydroxystearic acid; polyamide resins; condensates of an aromatic aldehyde and a polyhydric alcohol such as dibenzylidene-D-sorbitol; N-lauroyl-L-glutamic acid dibutylamide; cinnamic acids such as dicyclohexylammonium 4-chlorocinnamate, 3-chlorocinnamate, 4-bromocinnamate, 3-bromocinnamate, 4-methylcinnamate, silicon dioxide, glyceryl behenate; waxes; dextrin fatty acid esters; sucrose fatty acid esters; metal soaps; anhydrous silicic acids; (behenic acid/eicosanic diacid) glyceryl; or organically modified clay minerals may be chosen.

In a preferred embodiment, the oil gelator is 12-hydroxystearic acid, which is a fatty acid having a hydroxyl group. It can be obtained, for example, by hydrogenating a ricinoleic acid that is obtained from castor oil.

Exemplary wax oil gelators include paraffin wax, ceresin wax, microcrystalline wax, Fischer-Tropsch wax, polyethylene wax, carnauba wax or candelilla wax, or mixtures thereof. The marketed products thereof include trade name: Purified Carnauba Wax No. 1, produced by Noda Wax Co., Ltd.; trade name: OZOKERAITE WAX SP-273P, produced by STRAHL & PITSH INC.; trade name: Microwax 190Y, produced by Mobil Oil Co.; trade name: Himic 1080/2095, produced by Nippon Seiro Co., Ltd.; trade name: Sanwax E-200/E-300, produced by Sanyo Chemical Industries, Ltd.; trade name: Mobil 180, produced by Mobil Oil Co.; trade name: Starwax 100, produced by Bareco; trade name: Nisseki Microwax 180, produced by Nippon Oil Corporation; trade name: Fischer-Tropsch Wax FT-95/FT100H/FT-150/FT-200, produced by Sasol Wax Limited; trade name: BeSquare 180/185/190/195, produced by Bareco; trade name: Polywax 500/655, produced by Bareco; or trade name: Sasol Wax H1/C1/C2, produced by Sasol Wax Limited.

Exemplary dextrin fatty acid ester oil gelators include fatty acid esters that are soluble in oil and ester compounds of a linear or branched, saturated or unsaturated fatty acid(s) having 8 to 24 carbon atoms (preferably 14 to 18 carbon atoms) with a dextrin(s) having average degree of polymerization of 10 to 50 (preferably 20 to 30). They include dextrin palmitic acid, palm itic acid/2-ethylhexanoic acid dextrin, dextrin stearic acid, palmitic acid/stearic acid dextrin, dextrin oleic acid, dextrin isopalmitic acid, dextrin isostearic acid, or mixtures thereof. The marketed products of dextrin palm itic acid are, for example, trade name: Leopal KL, produced by Chiba Seifun Co., Ltd. or trade name: Leopal TL, produced by Chiba Seifun Co., Ltd. Further, the market products of palm itic acid/2-ethylhexanoic acid dextrin include trade name: Leopal TT, produced by Chiba Seifun Co., Ltd.

Exemplary sucrose fatty acid esters that are oil gelators include cosmetically acceptable sucrose fatty acid esters, particularly fatty acid esters of palmitic acid, stearic acid, behenic acid, oleic acid or lauric acid, or a mixture thereof.

Metal soaps that may also be used as oil gelators include isostearic acid aluminium, stearic acid aluminium or stearic acid calcium, or mixtures thereof.

Exemplary silicic acids that are oil gelators include fumy, porous, non-porous, or spherical silicic acids, or mixtures thereof. The marketed products of the anhydrous silicic acid are, for example, products of Nippon Aerosil Co., Ltd. (Aerosil 50, Aerosil 130, Aerosil 200, Aerosil 200V, Aerosil 200CF, Aerosil 200FAD, Aerosil 300, Aerosil 300CF and Aerosil 380). The hydrophobizing methods of the fumy anhydrous silicic acid are, for example, trimethylsiloxy treatment with trimethyl chlorosialane and hexamethyldisilazane, octyl silanization, coating and baking using methylhydrogen polysiloxane, and coating with metal soaps. Examples of the marketed products of the hydrophobized fumy anhydrous silicic acid are products of Nippon Aerosil Co., Ltd. (Aerosil R-972, Aerosil R-972V, Aerosil R-972CF, Aerosil R-974, Aerosil R-976S, Aerosil RX200, Aerosil RY200, Aerosil R-202, Aerosil R-805, Aerosil R-812, Aerosil RA200H); a product of Talco Co.: Taranox 500; or a product of Cabot Corporation: CAB-O-SIL TS-530.

Exemplary (behenic acid/eicosanic diacid) glyceryl oil gelling agents include oligomer esters of behenic acid and eicosanic diacid with glycerin. The marketed products thereof are, for example, trade name: Nomcort HK-G, by the Nisshin OilliO Group, Ltd.

Examples of organically modified clay mineral oil gelling agents include organically modified bentonites, water swell clay minerals treated with quaternary ammonium salts, or mixtures thereof. The marketed products of the organically modified bentonites are, for example, trade name: bentone 38, by NL Industries, Inc. and trade name: bentone 27 by NL Industries, Inc.

In an embodiment, the oil gelator includes the sodium and/or potassium salts of 12-hydroxystearic acid. In one or more embodiments, the oil gelator is 12-hydroxystearic acid.

It is possible to use one or a combination of oil gelators in compositions according to the disclosure.

According to various embodiments, the semi-solid gel may comprise from about 0.001% to about 5%, such as from about 0.01% to about 5%, from about 0.01% to about 4%, from about 0.01% to about 3%, from about 0.01% to about 2%, from about 0.01% to about 1%, from about 0.05% to about 5%, from about 0.05% to about 4%, from about 0.05% to about 3%, from about 0.05% to about 2%, from about 0.05% to about 1%, from about 0.1% to about 5%, from about 0.1% to about 4%, from about 0.1% to about 3%, from about 0.1% to about 2%, from about 0.1% to about 1%, or from about 0.1% to about 0.5% of at least one oil gelator, relative to the total weight of the composition.

Fatty Alcohols

The gelling oil phase comprises at least one fatty alcohol. In an embodiment, the fatty alcohol is a linear or branched, saturated or unsaturated $C_8$-$C_{30}$ alcohol, such as 2-butyloctanol, lauryl alcohol, 2-octyldodecanol, oleyl alcohol, isocetyl alcohol, isostearyl alcohol, stearyl alcohol, cetyl alcohol, behenyl alcohol, or a mixture thereof.

Fatty alcohols that can be used may be liquid at 25° C., 1 atm, or may even be solid. They may be glycerolated and/or oxyalkylenated, and may include from 8 to 30 carbon atoms. They may be saturated or unsaturated. The fatty alcohols useful herein include those having from about 8 to about 30 carbon atoms, from about 12 to about 22 carbon atoms, or from about 14 to about 22 carbon atoms. These fatty alcohols can be straight or branched chain alcohols and can be saturated or unsaturated. Nonlimiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol or a mixture thereof. In some cases, the fatty alcohols are those selected from the group consisting of myristyl alcohol, cetyl alcohol, stearyl alcohol, isostearyl alcohol, oleyl alcohol, isotridecyl alcohol, or a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, or 2-hexyldecanol.

The unsaturated liquid fatty alcohols include in their structure at least one double or triple bond and preferably one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol or undecylenyl alcohol can be cited.

In an embodiment, the fatty alcohol can be a fatty alcohol derivative. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl or stearyl alcohol, wherein the numeric designation indicates the number of ethylene glycol moieties present; C1-C30 alkyl ethers of the ceteth, steareth, or ceteareth compounds just described; polyoxyethylene ethers of branched alcohols such as octyldodecyl alcohol, dodecylpentadecyl alcohol, hexyldecyl alcohol, or isostearyl alcohol; polyoxyethylene ethers of behenyl alcohol; PPG ethers such as PPG-9-steareth-3, PPG-11 stearyl ether, PPG8-ceteth-1, or PPG-10 cetyl ether; or a mixture thereof.

In an embodiment, the at least one fatty alcohol is selected from myristyl alcohol, cetyl alcohol, stearyl alcohol or their mixture, cetylstearyl alcohol (or cetearyl alcohol), or mixtures thereof. In one embodiment, the at least one fatty alcohol is cetearyl alcohol.

According to various embodiments, a composition of the invention may comprise from about 0.01% to about 10%, such as from about 0.01% to about 7%, from about 0.01% to about 5%, from about 0.01% to about 3%, from about 0.01% to about 1%, from about 0.1% to about 5%, from about 0.1% to about 4%, from about 0.1% to about 3%, from about 0.1% to about 2%, from about 0.1% to about 1%, from about 0.5% to about 5%, from about 0.5% to about 4%, from about 0.5% to about 3%, from about 0.5% to about 2%, from about 0.5% to about 1%, from about 1% to about 5%, from about 1% to about 4%, from about 1% to about 3%, of at least one fatty alcohol relative to the total weight of the composition.

Fatty Compounds

As described herein, the gelling oil phase present according to various embodiments may include at least one fatty compound in addition to at least one fatty alcohol.

In various embodiments, the at least one fatty compound of the present invention are selected from (a) mono or polyglyceryl esters, (b) esters of fatty acid and fatty alcohol, (c) waxes and/or oils, (d) ethers; or (e) and optionally, hydrocarbons, carbonates, or am ides.

Fatty compounds that may be present include oils, mineral oil, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, or a mixture thereof.

Esters of fatty acids useful herein include esters of fatty acids having from about 8 to about 30 carbon atoms, from about 12 to about 22 carbon atoms, or from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of esters of fatty acids include esters of caprylic acid, caprate acid, lauric acid, myristic acid, palmitic acid, stearic acid, behenic acid, arichidonic acid, oleic acid, isostearic acid, sebacic acid, or mixtures thereof. In some cases, the fatty acids are selected from the group consisting of palm itic acid, myristic acid, caprate acid or caprylic acid or mixtures thereof.

Exemplary, non-limiting examples of esters of a fatty acid esters include esters of a $C_8$-$C_{30}$ fatty acid and a $C_1$-$C_{30}$ alcohol, ester of a $C_8$-$C_{30}$ fatty acid and a $C_8$-$C_{30}$ fatty alcohol, or esters of a $C_1$-$C_7$ acid or diacid and a $C_8$-$C_{30}$ fatty alcohol. Among these esters, mention may, for example, be made of ethyl, isopropyl, 2-ethylhexyl and 2-octyldecyl palmitate, isopropyl, butyl, cetyl or 2-octyldecyl myristate, butyl or hexyl stearate, hexyl or 2-hexyldecyl laurate, isononyl isononanoate, dioctyl malate, myristyl myristate, cetyl palmitate, isopropyl palmitate, or mixtures thereof.

Exemplary esters include polyglycerol esters of fatty acids include those of the following formula (XVII): For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

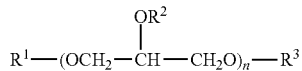

(XVII)

wherein:
the average value of n is about 3; and
$R^1$, $R^2$, and $R^3$, which may be identical or different, are independently chosen from a fatty acid moiety or hydrogen, provided that at least one of $R^1$, $R^2$, and $R^3$ is a fatty acid moiety.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, or mixtures thereof. Nonlimiting examples of fatty acid derivatives include ricinoleic acid, glycerol monostearate, ethyl stearate, cetyl stearate, cetyl palm itate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, or mixtures thereof.

In some embodiments the fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, or 50° C. or higher. The high melting point fatty compound may be selected from fatty acids, fatty alcohol derivatives, fatty acid derivatives, or mixtures thereof. Nonlimiting examples of the high melting point compounds are found in the International Cosmetic Ingredient Dictionary, Sixteenth Edition, 2016, which is incorporated by reference herein in its entirety.

In one embodiment, the at least one ester of a fatty acid and/or at least one ester of an alcohol is chosen from isopropyl myristate, isopropyl palmitate, cetyl palmitate, coco-caprylate/caprate, or mixtures thereof.

According to various embodiments, a composition of the invention may comprise from about 15% to about 35%, such as from about 18% to about 32%, from about 20% to about 32%, from about 20% to about 30%, of at least one fatty compound, relative to the total weight of the composition.

In an exemplary embodiment, the gelling oil phase comprises at least one ester of glycerin and fatty acid, also referred to as "fatty acid glycerides." "Fatty acid glycerides" are fats or oils in which the fatty acid contains 6 to 24 carbon atoms. Non-limiting examples of natural fatty acid glycerides includes avocado oil, wheatgerm oil, argan oil, peanut oil, sesame oil, sunflower seed oil, olive oil, palm oil, coconut oil, hazelnut oil, apricot oil, macadamia oil, arara oil, castor oil, corn oil, cottonseed oil, rapeseed oil, linseed oil, soybean oil, tung oil, fish oils, sweet almond oil, safflower oil, candlenut oil, camellina oil, tamanu oil, babassu oil and pracaxi oil, or mixtures thereof.

In one embodiment, the at least ester of glycerin and fatty acid is chosen from caprylic/capric triglyceride, glyceryl stearate, or mixtures thereof.

According to various embodiments, a composition of the invention may comprise from about 0.1% to about 10%, such as from about 1% to about 10%, from about 2% to about 10%, from about 3% to about 10%, from about 2% to about 8%, from about 3% to about 8%, from about 2% to about 7%, from about 2% to about 6%, from about 2% to about 5%, from about 3% to about 5%, or from about 3% to about 4% by weight, of at least one ester of glycerin and fatty acid relative to the total weight of the composition.

Non-limiting examples of additional fatty compounds include plant oils and liquid emollients such as hydrogenated vegetable oil and cocoa seed butter. For example, fatty compounds that may be useful may be chosen from (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic plant extracts; (e) hydrocarbons such as liquid paraffins, vaseline, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; (j) lipids such as cholesterol, ceram ides, sucrose esters and pseudo-ceram ides as described in European Patent Specification No. 556,957; (k) vitamins, minerals, and skin nutrients such as vitamins A, E, and K; vitamin alkyl esters, including vitamin C alkyl esters; magnesium, calcium, and milk. (l) sunscreens such as octyl methoxyl cinnamate (Parsol MCX) and butyl methoxy benzoylmethane (Parsol 1789); (l) phospholipids; (m) polyhydric alcohols such as glycerine and propylene glycol; and polyols such as polyethylene glycols, (n) anti-aging compounds such as alpha hydroxy acids, beta hydroxy acids; and (o) mixtures of any of the foregoing components, and the like.

In one embodiment, the at least one fatty compound is chosen from plant oils. In further embodiments, the at least one fatty compound is chosen from hydrogenated vegetable oil, cocoa seed butter, or dicaprylyl ether or a mixture thereof.

According to various embodiments, a composition of the invention may comprise from about 0.01% to about 10%, such as from about 0.01% to about 8%, from about 0.1% to about 10%, from about 0.1% to about 8%, from about 0.5% to about 10%, from about 0.5% to about 8%, from about 0.5% to about 6%, from about 0.1% to about 5%, from about 0.5% to about 5%, from about 1% to about 5%, or from about 1 to about 3% by weight, of at least one fatty compound relative to the total weight of the composition.

Aqueous Gel Phase

According to various exemplary embodiments of the disclosure, the aqueous phase of the semi-solid gel composition is a lamellar crystalline aqueous gel phase comprising: i) water and optionally at least one polyol present in an amount up to about 50% by weight, relative to the weight of the total composition; ii) at least one lamellar crystalline phase structurant; and iii) at least one emulsifier such as polyglyceryl esters.

The lamellar crystalline aqueous gel phase may, according to various embodiments, be present in the semi-solid gel in an amount ranging from less than about 50%, such as less than about 49%, less than about 48%, less than about 47%, less than about 46%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, or less than about 30% by weight relative to the total weight of the composition. By way of non-limiting example, the aqueous gel component may be present in an amount ranging from about 30% to about 50%, about 35% to about 50%, about 36% to about 48%, about 35% to about 45%, or about 35% to about 42% by weight relative to the total weight of the composition.

Water and/or Polyol

As described herein, the lamellar crystalline gel phase present according to various embodiments may include water and/or at least one polyol.

As used herein, the term "polyol" means an organic compound comprising at least two hydroxyl groups (—OH), borne by different carbon atoms, this compound possibly being aliphatic, acyclic, linear or branched.

In various embodiments, the at least one polyol that may be used according to embodiments of the disclosure comprises from about 2 to about 30 hydroxyl groups, such as from about 2 to about 10 hydroxyl groups, or from 2 to 3 hydroxyl groups. According to certain embodiments, the at least one polyol comprises at least three carbon atoms.

In various embodiments, the at least one polyol is chosen from polyols comprising at least three carbon atoms and ethylene glycol, for example propylene glycol, butylene glycol, 1,3-propanediol, 1,3-butylene glycol, 1,2-pentanediol, dipropylene glycol, hexylene glycol, pentylene glycol, glycerol, ethylene glycol, or mixtures thereof.

According to some embodiments, the at least one polyol is chosen from propylene glycol, 1,3-propanediol, or mixtures thereof. In certain embodiments, the at least one polyol is chosen from butylene glycol or glycerin.

In an embodiment, the water and/or at least one polyol present in an amount up to about 50 wt %, up to about 49%, up to about 48%, up to about 47%, up to about 46%, up to about 45%, up to about 44%, up to about 43%, up to about 42%, up to about 41%, up to about 40%, up to about 39%, up to about 38%, up to about 37%, up to about 36%, up to about 35%, up to about 34%, up to about 33%, up to about 32%, up to about 31%, or up to about 30%, by weight, relative to the weight of the total composition.

Crystalline Phase Structurant

As described herein, the lamellar crystalline gel phase present according to various embodiments includes at least one crystalline phase structurant. Exemplary lamellar crystalline gel embodiments include mixtures of hydrophilic and hydrophobic crystalline surfactants and soluble or swellable polymers. These structurants normally contain saturated C12-22 chains and have melting points above 55 C.

Exemplary hydrophobic structurants include Cetyl, Stearyl, Behenyl alcohols, Stearic acid, Steareth 2, Sorbitan Stearate, and Glyceryl Stearate. Exemplary anionic hydrophilic structurants include neutralized fatty acid soaps, Sodium Stearoyl Glutamate, Sodium Stearoyl Lactylate, and Potassium Cetyl Phosphate. Exemplary cationic structurants include Behentrimonium Chloride and Distearyl Dimethyl Ammonium Chloride. Exemplary nonionics include Steareth 20, PEG 40 Stearate, PEG 100 Stearate, Polysorbate 60, Cetearyl Glucoside.

In exemplary embodiments, the crystalline phase structurant is sodium stearoyl glutamate.

In an embodiment, the structured lamellar crystalline gel phase further comprises a thickener. In one embodiment, the structured lamellar crystalline gel phase further comprises a natural thickener is chosen from gums, polysaccharides, or mixtures thereof.

In an embodiment, the at least one crystalline phase structurant is present in an amount up to about 5%, such as up to about 4%, up to about 3%, up to about 2%, up to about 1%, or up to about 0.5% by weight, such as, for example, from about 0.001% to about 5%, about 0.001% to about 4%, about 0.001% to about 3%, about 0.001% to about 2%, or about 0.001% to about 1% by weight, relative to the total weight of the composition. For example, the crystalline phase structurant may be present in an amount ranging from about 0.01% to about 5%, about 0.01% to about 4%, about 0.01% to about 3%, about 0.01% to about 2%, or about 0.01% to about 1% by weight, relative to the total weight of the composition.

Emulsifier

As described herein, the lamellar crystalline gel phase present according to various embodiments may include at least one emulsifier chosen from polyoxyethylene alkyl ether carboxylic acids, such as Laureth-5 Carboxylic Acid, ethers of a sugar and of $C_8$-$C_{24}$ fatty alcohols, such as caprylyl/capryl glucoside, polyoxyethylenated fatty alcohol containing from 6 to 12 oxyethylene units, such as Laureth-9, polyoxyalkylenated derivative of mono glyceryl ester of a fatty acid such as PEG-20 glyceryl triisostearate, mono and polyglyceryl esters of a fatty acid, sarcosinates, such as sodium lauroyl sarcosinate, or mixtures thereof.

As polyglyceryl esters of (a) fatty acid(s), mention be made of the product containing 2 to 10 glycerol units, such as polyglyceryl monolaurate, oleate, myristate, caprylate, or stearate comprising 2 to 10 glycerol units, polyglyceryl mono(iso)stearate comprising 2 to 10 glycerol units, polyglyceryl dioleate comprising 2 to 10 glycerol units, polyglyceryl dilaurate comprising 2 to 10 glycerol units, polyglyceryl dimyristate comprising 2 to 10 glycerol units, polyglyceryl trimyristate comprising 2 to 10 glycerol units, polyglyceryl trioleate comprising 2 to 10 glycerol units, and polyglyceryl tricaprylate comprising 2 to 10 glycerol units.

In an exemplary embodiment, polyglyceryl esters can be used and include, polyglyceryl esters of $C_{16}$-$C_{22}$ saturated, unsaturated and branched chain fatty acids, such as polyglyceryl-4 isostearate, polyglyceryl-3 oleate, polyglyceryl-2 oleate, polyglyceryl-2 sesquioleate, triglyceryl diisostearate, diglyceryl monooleate, tetraglyceryl monooleate, or mixtures thereof.

Emulsifiers may be selected from esters of polyols with fatty acids with a saturated or unsaturated chain containing for example from 8 to 24 carbon atoms, preferably 12 to 22 carbon atoms, or polyoxyalkylenated derivatives thereof, preferably containing from 10 to 200, or more preferably from 10 to 100 oxyalkylene units, such as mono glyceryl esters or poly glyceryl esters of a $C_8$-$C_{24}$, preferably $C_{12}$-$C_{22}$, fatty acid or acids and polyoxyalkylenated derivatives thereof, preferably containing from 10 to 200, or more preferably from 10 to 100 oxyalkylene units; sorbitol esters of a $C_8$-$C_{24}$, preferably $C_{12}$-$C_{22}$, fatty acid or acids or polyoxyalkylenated derivatives thereof, preferably containing from 10 to 200, or more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids or polyoxyalkylenated derivatives thereof, preferably containing from 10 to 200, or more preferably from 10 to 100 oxyalkylene units; ethers of fatty alcohols; ethers of sugar and a $C_8$-$C_{24}$, preferably $C_{12}$-$C_{22}$, fatty alcohol or alcohols; or mixtures thereof.

In an exemplary embodiment, the monoglyceryl esters that can be used and include, but are not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, or mixtures thereof.

As mono glyceryl esters of fatty acids, glyceryl stearate (glyceryl mono-, di- and/or tristearate) (CTFA name: glyceryl stearate) or glyceryl ricinoleate or mixtures thereof can be cited, or as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di-, tristearate and/or triisostearate) can be cited. Preferably, the polyoxyalkylenated derivative of mono glyceryl ester of fatty acids includes 10 to 40 oxyethylene units, such as PEG-20 glyceryl triisostearate.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, or sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, or mixtures thereof, can for example be cited.

As sucrose esters, saccharose palmito-stearate, saccharose stearate and saccharose monolaurate can for example be cited.

As sugar ethers, alkylpolyglucosides can be used, and for example, ethers of a sugar and of $C_8$-$C_{24}$ fatty alcohols including decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, or mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or a branched $C_{12}$-$C_{22}$ acyl chain such as an oleyl or isostearyl group.

According to one of the embodiments according to the present invention, the nonionic surfactant may be selected from copolymers of ethylene oxide and of propylene oxide, in particular copolymers of the following formula: $HO(C_2H_4O)_a(C_3H_6O)_b(C_2H_4O)_cH$ in which a, b and c are integers such that a+c ranges from 2 to 100 and b ranges from 14 to 60, or mixtures thereof.

Preferably, the emulsifier used in the composition according to the present invention can be selected from a group consisting of, ethers of a sugar and of $C_8$-$C_{24}$ fatty alcohols, such as caprylyl/capryl glucoside, polyoxyethylenated fatty alcohol containing from 6 to 12 oxyethylene units, such as Laureth-9, polyoxyalkylenated derivative of mono glyceryl ester of a fatty acid, such as PEG-20 glyceryl triisostearate, and polyglyceryl esters of a fatty acid, such as polyglyceryl-6 distearate, polyglyceryl-4 isostearate, or mixtures thereof.

In some instances, the fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

In one embodiment, the composition includes waxes. Mention may be made, among the waxes capable of being used as non-silicone fatty compounds, of animal waxes, such as beeswax; vegetable waxes, such as sunflower seed (*Helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the fatty compounds include one or more oils. The term "oil" as used herein describes any material which is substantially insoluble in water. Exemplary oils include, but are not limited to, natural oils, such as coconut oil; hydrogenated vegetable oils, hydrocarbons, such as mineral oil and hydrogenated polyisobutene. Exemplary low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palm itate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized in an embodiment. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are semi-solid at 25° C., such as hydrogenated castor, palm or coconut oils, or hydrogenated tallow; mono-, di-, tri- or sucroglycerides; lanolins; or fatty esters which are semi-solid at 25° C.

In various embodiments, the gelling oil phase optionally further comprises at least one other ester. For example, in various embodiments, the gelling oil phase further comprises at least one other ester chosen from jojoba esters, polyglyeryl-3 beeswax, or mixtures of thereof.

In one embodiment, the composition further comprises dicaprylyl ether.

In one embodiment, a combination of emulsifiers may be used.

In an embodiment, the at least one emulsifier may be present in an amount up to about 10%, up to about 9%, up to about 8%, up to about 7%, up to about 6%, up to about 5%, or up to about 4%, such as from 0.1% to 10%, from 0.1% to 9%, from 0.1% to 8%, from 0.1% to 7%, from 0.1% to 6%, from 0.1% to 5%, or from 0.1% to 4%, by weight relative to the total weight of the composition. For example, the at least one emulsifier may be present in an amount ranging from about 2% to about 8%, about 3% to about 7%, or about 4% to about 6%, or about 2% to about 5%, by weight relative to the total weight of the composition.

Additional Ingredients

The composition according to the disclosure may also comprise additives chosen from nacreous agents, dyes or pigments, fragrances, mineral, plant or synthetic oils, waxes, vitamins, proteins including ceramides, vitamins, UV-screening agents, free-radical scavengers, antidandruff agents, hair-loss counteractants, hair restorers, preserving agents, or mixtures thereof. A person skilled in the art will take care to select the optional additives and the amount thereof such that they do not harm the properties of the compositions of the present disclosure.

The compositions of certain embodiments may comprise stabilizers, for example sodium chloride, magnesium dichloride or magnesium sulfate.

The compositions according to the disclosure may additionally comprise cosmetic adjuvants chosen from fragrances, pigments, chelating agents, softeners, antioxidants, opacifiers, stabilizers, moisturizing agents, vitamins, bactericides, preservatives, polymers, thickening agents, or any other ingredient commonly used in cosmetics for this type of application.

These ingredients can be synthetic or naturally-sourced such as from plants. In certain embodiments, at least 75%, such as at least 80%, at least 85%, at least 90%, or at least 95% of the materials used in the composition are plant-based. In an embodiment, compositions according to the disclosure may have all these improved properties while comprising mostly, such as at least 95%, natural origin ingredients.

In present in the composition, these additives are generally present in an amount ranging up to about 40% by weight of active material relative to the total weight of the composition, such as up to about 30%, up to about 20%, up to about 15%, up to about 10%, up to about 5%, such as from 0% to 30%.

The amounts of these various constituents which can be present in the composition according to the disclosure are those conventionally used in the art. The composition according to the disclosure especially finds a particularly advantageous application in the hair sector, especially for caring for the hair or the scalp. The hair compositions are preferably hair or skin oils, conditioners, care creams, balms, and/or masks. Preferably, the composition according to the disclosure is a leave-in treatment.

In some cases, the compositions are free or substantially free of silicones. For example, the compositions include less than about 3 wt. %, 2 wt. %, 1 wt. %, or 0.5 wt. % of silicones (preferably no silicones). In some cases, the compositions comprise silicones. Non-limiting examples of silicones include amine-functionalized silicones (e.g., amodimethicone), dimethicone, bis-aminopropyl dimethicone, trimethyl silylamodimethicone, etc.

The composition according to the disclosure may be contained in a jar, a tube or in a bottle optionally equipped with a pump, or any suitable packages.

Advantageously, the composition according to the disclosure is in the form of a solid/semi-solidgel/cream/balm/paste leave-in treatment.

Methods of Making a Semi-Solid Gel

According to various embodiments of the disclosure, stable lamellar crystal semi-solid oil gels/cream/balm can be prepared by any appropriate method. For example, as disclosed herein, stable lamellar crystal semi-solid gels can be prepared by mixing the disclosed gelling oil phase and the disclosed lamellar crystalline gel phase according to various embodiments.

As used herein, the term "high-pressure homogenizer" and variations thereof is intended to denote use of a homogenizer operating under a pressure ranging from about 150 to about 1250 bar, for example from about 250 bar to about 1250 bar, from about 400 to about 1000 bar, or from about 500 to about 800 bar.

As used herein, the term "mixing" is intended to mean any process by which the components are combined in such a way as to make a mixture thereof that is substantially uniform throughout.

In at least one embodiment, the semi-solid gel is made by combining the gelling oil phase and the lamellar crystalline gel phase, and then mixing at a speed that allows homogenization. In one embodiment, the mixture is subjected to high-pressure homogenization. In yet a further embodiment, the semi-solid gel emulsion is prepared by combining all components into a high-pressure homogenizer and homogenizing the components all together at once. In certain embodiments, the mixture can be subjected to the high-pressure homogenization process more than once, such as from 2 to 20 times or more. In an embodiment, the homogenization results in a homogenized, white opaque emulsion. In certain embodiments, the mixture is mixed for at least about 1, 2, or 3 minutes. Alternatively, or in addition, homogenization can be carried out under ultrasound.

In an exemplary embodiment, the gelling oil phase and the lamellar crystalline gel phase are heated prior to mixing. In an exemplary embodiment, the gelling oil phase is heated to a temperature of at least 80° C. In an exemplary embodiment, the lamellar crystalline gel phase is heated to a temperature of at least 80° C.

By way of example only, a semi-solid gel emulsion may be prepared by stirring the gelling oil phase and the lamellar crystalline gel phase by any method, e.g. in any mixer, at a rate of between about 500 and 5000 rpm, for a period of time ranging from about 5 to about 30 minutes, at a temperature ranging from about 20° C. to about 95° C.

According to at least certain exemplary embodiments, the semi-solid gel emulsions prepared according to the disclosure are stable. As used herein, the terms "stable" and "stabilize," as well as variations thereof, are intended to mean that the gel shows no phase separation as perceptible to the human eye after one week at ambient pressure and a temperature of either room temperature or 45° C.

The above exemplified methods are not intending to be limiting; rather, any method is contemplated wherein the gelling oil phase and the lamellar crystalline gel phase can be prepared into a stable lamellar crystalline oil gel, whereby the gel is partly or completely stabilized by the lamellar crystalline aqueous phase.

In various embodiments, the compositions described herein may have a pH ranging from about 2 to about 9, such as about 3 to about 8, or about 4 to about 7.

Methods of Use

According to various embodiments, methods of treating keratinous substrates, wherein said method involves applying onto keratinous substrates the semi-solid gel compositions of the present disclosure as described herein.

According to various exemplary embodiments, the semi-solid gel compositions may be applied directly to a keratinous substrate, such as the hair or the skin, or shear forces may be applied to the compositions prior to application. Shear forces include the application of an external stimuli, for example physical force, such as rubbing. For example, the composition may be applied to the keratinous substrate by first applying to the hands, rubbing the hands together to apply a shear force to the semi-solid gel composition, e.g. to transform the semi-solid gel composition to a liquid gel composition, and then contacting the keratinous substrates with the hands.

By way of example only, before, during, or after the semi-solid gel compositions is applied to wet or dry keratinous substrate, the keratinous substrates may be further treated with said external stimuli. In at least certain embodiments, if the keratinous substrate is hair, the hair may also be styled, shaped, or positioned as desired, optionally while exposed to external stimuli, such as brushing or combing or running the fingers through the hair. The above-described methods may additionally include one or more steps of treating hair using a means for treating hair.

In an embodiment, the method comprises mechanically shearing the composition prior to applying it to the keratinous substrate. In another embodiment, the method comprises mechanically shearing the composition while applying it to the keratinous substrate.

In addition, hair treated with the semi-solid gel compositions according to the disclosure may, in at least certain exemplary embodiments, be hydrophobic, and/or may appear less frizzy and/or may be less prone to breakage, and/or may be more moisturized, and/or may have more grip when blow drying, and/or may be smoother, and/or may have a more natural or "clean" feeling, and and/or may have less static relative to hair not having been treated with a composition according to the disclosure.

It should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

The compositions may be applied to wet or dry keratinous substrates. As used herein, the methods/processes and compositions disclosed herein may be used on the hair that has or has not been artificially dyed, pigmented or permed. The method/process and composition disclosed herein may be used on any type of hair, including African American and Caucasian hair.

The compositions described throughout this disclosure may be a "leave-on" product. A "leave-on" (also called leave-in) product refers to a composition that is applied to keratinous substrates such as hair or skin and is not subjected to immediate rinsing and/or washing for at least 4 hours or for a period of time ranging from 4 hours up to 72 hours, from 4 hours up to 48 hours, or from 8 hours up to 36 hours, or from 8 hours up to 24 hours. In other words, the product is applied to the substrate such as hair, for example, and remains on the hair, as styled, i.e., it is not removed from the hair prior to styling the hair.

The compositions described throughout this disclosure may be a "risne-off" product. A "rinse-off" (also called rinse-out) product refers to a composition that is applied to keratinous substrates such as hair or skin and is rinsed from the substrate after treating substrate for a short period of time such as for about 30 seconds, or for about 1 minute or for about 5 minutes, or for about 10 minutes, or for about 20 minutes, or for about 30 minutes, or up to about an hour.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5%, 4%, 3%, 2%, or 1% of the indicated number. Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, parts and ratios herein are relative to the amount of active agent, based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

It should also be understood that the precise numerical values used in the specification and claims form additional embodiments of the disclosure, and are intended to include any ranges which may be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

The term "synthetic" means a material that is not of natural origin. The term "natural," "naturally based," and "naturally-sourced" means a material of natural origin, such as derived from plants, which also cannot be subsequently chemically or physically modified. "Plant-based" means that the material came from a plant.

"Treated," "cosmetically treated," "treating," and the like means to improve or restore appearance, feel, resistance to breakage, etc.

The compositions and methods of the present disclosure can comprise, consist of, or consist essentially of the essential elements and limitations of the disclosure described herein, as well as any additional or optional ingredients, components, or limitations described herein or otherwise useful.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

All patents and publications are expressly incorporated herein in their entireties.

EXAMPLES

The following examples serve to illustrate the embodiments of the disclosure without however exhibiting a limiting character. The Examples are intended to be non-restrictive and explanatory only, with the scope of the invention being defined by the claims. In these examples the amounts of the composition ingredients are given as weight percentages of active ingredients relative to the total weight of the composition.

Example 1

A composition comprising a gelling oil phase and a lamellar crystalline gel phase was prepared as follows.

Water, polyol, and sodium stearoyl glutamate were mixed in a first kettle and heated up to a temperature of 80° C. Additionally, 12-hydroxylstearic acid, isopropyl myristate, cetyl alcohol, caprylic/capric triglyceride, cococaprylate/caprate, cetyl palmitate, cocoa seed butter, dicaprylyl ether, hydrogenated vegetable oil, glyceryl stearate, and a mixture of polyglyceryl-6 distearate and jojoba esters and cetyl alcohol and polyglyceryl-3 bees wax were mixed in a second kettle and heated up to a temperature of 80° C. Once both mixtures melted into liquids, the mixture in the second kettle was slowly poured into the first kettle at 80° C. and homogenized, which resulted in a white opaque emulsion. The emulsion was mixed for additional 2-3 minutes thoroughly after the mixtures were combined. The emulsion was cooled to 65° C., then poured into a jar for dispensing at 50-60° C. to finish cooling at room temperature.

Example 2

Compositions comprising a gelling oil phase and a lamellar crystalline gel phase with the following ingredients were prepared and are disclosed in Table 1 below:

TABLE 1

| US INCI NAME | Inventive Compositions | | | |
|---|---|---|---|---|
| | A | B | C | D |
| CAPRYLIC/CAPRIC TRIGLYCERIDE | 2 | 5 | 5 | 2 |
| GLYCERYL STEARATE | 1.5 | 3 | 1 | 1 |
| CETYL ESTERS | | | 0.9 | 0.9 |
| CETYL ESTERS | | | 0.6 | 0.6 |
| POLYGLYCERYL-6 DISTEARATE | 2.24 | 2.56 | 1.6 | 1.92 |
| POLYGLYCERYL-3 BEESWAX | 0.30 | 0.34 | 0.21 | 0.26 |
| HYDROXYSTEARIC ACID | 0.3 | 0.2 | 0.5 | 0.5 |
| ISOPROPYL MYRISTATE | 25 | 18 | 22.5 | 25 |
| CETYL ALCOHOL | 0.30 | 0.34 | 0.21 | 0.26 |
| SODIUM STEAROYL GLUTAMATE | 0.15 | 0.1 | 0.1 | 0.1 |
| GLYCERIN | 12 | 15 | 10 | 12 |
| DICAPRYLYL ETHER | 22.49 | 17.99 | 22.49 | 22.49 |
| CETEARYL ALCOHOL | 2.5 | 1 | 2.5 | 2.5 |
| HYDROGENATED VEGETABLE OIL | 2 | 5 | | |
| WATER | 22.55 | 26.70 | 24.2 | 22.2 |
| HELIANTHUS ANNUUS (SUNFLOWER) SEED OIL | 0.01 | 0.01 | | |
| THEOBROMA CACAO (COCOA) SEED BUTTER | | 1 | 0.5 | 0.5 |
| POLYGLYCERYL-4 ISOSTEARATE | 2 | | 2 | 2 |
| COCO-CAPRYLATE/CAPRATE | 2 | | 5 | 5 |
| CETYL PALMITATE | 1.5 | 2.5 | | |
| JOJOBA ESTERS | 0.67 | 0.76 | 0.48 | 0.57 |

Example 3

The following Comparative Composition in Table 2 was prepared:

TABLE 2

| US INCI NAME | Comparative Composition F |
|---|---|
| ASTROCARYUM MURUMURU SEED BUTTER | 0.10 |
| CETYL ESTERS | 0.43 |
| CETYL ESTERS | 0.29 |

TABLE 2-continued

| US INCI NAME | Comparative Composition F |
|---|---|
| MANGIFERA INDICA (MANGO) SEED BUTTER | 0.1 |
| BENZYL ALCOHOL | 1 |
| ISOPROPYL MYRISTATE | 6 |
| GLYCERYL STEARATE SE | 4 |
| XANTHAN GUM | 0.00015 |
| CAPRYLYL GLYCOL | 0.5 |
| POTASSIUM SORBATE | 0.0001 |
| HYDROXYPROPYL GUAR | 0.2 |
| CETEARYL GLUCOSIDE | 0.5 |
| GLYCERIN | 5.05 |
| CETEARYL ALCOHOL | 10 |
| WATER | 63.62713 |
| COCOS NUCIFERA (COCONUT) FRUIT EXTRACT | 0.00262 |
| COCOS NUCIFERA (COCONUT) OIL | 0.1 |
| BEESWAX | 6.6 |

The hair of 10 volunteers was shampooed, rinsed and wrung out to remove excess water. Inventive Composition A, a semi-solid gel paste leave-in oil hair treatment composition comprising a gelling oil phase and a lamellar crystalline gel phase composition, was tested and compared to Comparative Composition F, a cream leave-in oil hair treatment composition without a lamellar crystalline gel phase. Inventive Composition A was dispensed and rubbed between two hands and applied to hair on half of the volunteers' heads, starting from the hair ends (tips), Comparative Composition F was similarly dispensed, rubbed and applied on the other half of the volunteers' heads.

Inventive Composition A dispensed as a semi-solid gel paste (i.e. a balm or a cream), and instantly transformed into a liquid oil upon rubbing, creating a favorable melting sensation in the hands. Comparative Composition F was dispensed as a cream, and did not melt into an oil upon rubbing.

The hair was then brushed and blow-dried. Inventive Composition A was easier to distribute to the ends, was absorbed better by the hair, felt less sticky on the hair, and left less coating on the hair/left less residue than Comparative Composition F. These improvements were achieved with less product than Comparative Composition F. These changes were observed more quickly than with Comparative Composition F. Wet hair treated with Inventive Composition A was easier to detangle. Once dry, hair treated with Inventive Composition A was more supple and smooth.

Example 4

The following Comparative Composition in Table 3 was prepared:

TABLE 3

| US INCI NAME | Comparative Composition G |
|---|---|
| ARGANIA SPINOSA KERNEL OIL | 0.1 |
| CYCLOPENTASILOXANE | 92.34 |
| DIMETHICONOL | 7.35 |
| HELIANTHUS ANNUUS (SUNFLOWER) SEED OIL | 0.002 |

The hair of 10 volunteers was shampooed, detangled, rinsed and wrung out to remove excess water. Inventive Composition A was tested and compared to Comparative Composition G, a liquid leave-in oil hair treatment composition without a lamellar crystalline gel phase. Inventive Composition A was dispensed and rubbed between two hands and applied to hair on half of the volunteers' heads, starting from the hair ends (tips), Comparative Composition G was similarly dispensed, rubbed and applied on the other half of the volunteers' heads.

As in Example 2, Inventive Composition A dispensed as a semi-solid gel paste, and instantly transformed into a liquid oil upon rubbing, creating a favorable melting sensation in the hands. Comparative Composition G was dispensed as a liquid oil serum and did not change phases upon rubbing.

Inventive Composition A and Comparative Composition F displayed no noticeable differences in cosmeticity.

The invention claimed is:

1. A semi-solid gel composition comprising:
   (a) a gelling oil phase comprising:
      (i) at least one oil gelator;
      (ii) at least one fatty alcohol;
      (iii) at least one fatty compound other than the (ii) fatty alcohol(s);
      wherein said gelling oil phase is present in an amount of from at least about 50% by weight, relative to the weight of the total composition; and
   (b) a lamellar crystalline aqueous gel phase comprising:
      (i) water and optionally at least one polyol, wherein the water and optional polyol present in a total amount up to about 50% by weight, relative to the weight of the total composition;
      (ii) at least one lamellar crystalline phase structurant; and
      (iii) at least one emulsifier,
   wherein the semi-solid gel composition has a transformative texture that permits the gel to transform to a liquid under a shear force.

2. The semi-solid gel composition of claim 1, wherein the gelling oil phase is dispersed in the lamellar crystalline aqueous gel phase.

3. The semi-solid gel composition of claim 1, wherein the lamellar crystalline aqueous gel phase is continuous.

4. The semi-solid gel composition of claim 1, wherein the oil gelator is chosen from esters and/or amides of fatty acid gellants, hydroxy acids, hydroxy fatty acids and/or derivatives thereof and/or salts thereof, cholesterolic materials, lanolinolic materials, other amide gellants, crystalline gellants, or mixtures thereof.

5. The semi-solid gel composition of claim 1, wherein the oil gelator is chosen from hydroxy fatty acids and/or derivatives thereof and/or salts thereof selected from 12-hydroxystearic acid and/or salts thereof, esters of 12-hydroxystearic acid, amides of 12-hydroxystearic acid or mixtures thereof.

6. The semi-solid gel composition of claim 1, wherein the at least one fatty alcohol is chosen from a linear or branched, saturated or unsaturated $C_8$-$C_{30}$ alcohol.

7. The semi-solid gel composition of claim 1, wherein the at least one fatty alcohol is chosen from cetearyl alcohol, 2-butyloctanol, lauryl alcohol, 2-octyldodecanol, oleyl alcohol, isocetyl alcohol, isostearyl alcohol, stearyl alcohol, cetyl alcohol, behenyl alcohol, or mixtures thereof.

8. The semi-solid gel composition of claim 1, wherein the at least one fatty compound is chosen from (a) mono or polyglyceryl esters, (b) esters of fatty acid and fatty alcohol, (c) waxes and/or oils, (d) ethers, (e) hydrocarbons, carbonates, and/or amides, or mixtures thereof.

9. The semi-solid gel composition of claim 1, wherein the at least one fatty compound is chosen from isopropyl myristate, isopropyl palmitate, cetyl palmitate, coco-caprylate/caprate, caprylic/capric triglyceride, glyceryl stearate, glyceryl oleate, glyceryl caprate, glyceryl caprylate, or mixtures thereof.

10. The semi-solid gel composition of claim 1, wherein the at least one fatty compound is chosen from plant oils, vegetable oil, cocoa seed butter, dicaprylyl ether, or mixtures thereof.

11. The semi-solid gel composition of claim 1, wherein the lamellar crystalline phase structurant is chosen from Cetyl alcohol, Stearyl alcohol, Behenyl alcohol, Stearic acid, Steareth 2, Sorbitan Stearate, Glyceryl Stearate, Sodium Stearoyl Glutamate, Sodium Stearoyl Lactylate, Potassium Cetyl Phosphate, Steareth 20, PEG 40 Stearate, PEG 100 Stearate, Polysorbate 60, Cetearyl Glucoside, or mixtures thereof.

12. The semi-solid gel composition of claim 1, wherein the lamellar crystalline phase structurant is sodium stearoyl glutamate.

13. The semi-solid gel composition of claim 1, wherein the lamellar crystalline phase emulsifier is chosen from polyoxyethylene alkyl ether carboxylic acids, ethers of a sugar and of $C_8$-$C_{24}$ fatty alcohols, polyoxyethylenated fatty alcohol containing from 6 to 12 oxyethylene units, polyoxyalkylenated derivative of mono glyceryl ester of a fatty acid, mono or polyglyceryl esters of a fatty acid, sarcosinates, or mixtures thereof.

14. The semi-solid gel composition of claim 1, wherein the lamellar crystalline phase emulsifier is a polygylceryl ester chosen from polyglyceryl esters of $C_{16}$-$C_{22}$ saturated, unsaturated and branched chain fatty acids, such as polyglyceryl-4 isostearate, polyglyceryl-3 oleate, polyglyceryl-2 oleate, polyglyceryl-2 sesquioleate, triglyceryl diisostearate, diglyceryl monooleate, tetraglyceryl monooleate, or mixtures thereof.

15. The semi-solid gel composition of claim 1, further comprising a natural thickener chosen from natural gums, polysaccharides, or mixtures thereof.

16. The semi-solid gel composition of claim 1, wherein the wherein the weight ratio of water to the at least one polyol ranges from 1:2 to 1:0.

17. A semi-solid gel composition comprising:
   (a) a gelling oil phase comprising:
      (i) 12-hydroxystearic acid;
      (ii) cetearyl alcohol;
      (iii) at least one ester of a fatty acid and an alcohol chosen from isopropyl myristate, cetyl palmitate, coco-caprylate/caprate, or mixtures thereof;
      (iv) at least one ester of glycerin and fatty acids chosen from caprylic/capric triglyceride, glyceryl stearate, or mixtures thereof; and
      (v) at least one fatty compound chosen from plant oils, hydrogenated vegetable oil, cocoa seed butter, dicaprylyl ether or mixtures thereof;
      wherein said gelling oil phase is present in an amount of from at least about 50% by weight, relative to the weight of the total composition; and
   (b) a lamellar crystalline aqueous gel phase comprising:
      (i) water and/or at least one polyol present in an amount up to about 50% by weight, relative to the weight of the total composition;
      (ii) sodium stearoyl glutamate; and
      (iii) at least one emulsifier chosen from polyglyceryl-4 isostearate, polyglyceryl-6 distearate, or mixtures thereof,
   wherein the semi-solid gel composition has a transformative texture that permits the gel to transform to a liquid under a shear force.

18. A method for treating a keratinous substrate, said method comprising transforming a semi-solid gel composition to a liquid by applying a shear force to the semi-solid gel composition and subsequently applying the liquid to the keratinous substrate, the semi-solid gel composition comprising:
- (a) a gelling oil phase comprising:
  - (i) at least one oil gelator;
  - (ii) at least one fatty alcohol; and
  - (iii) at least one fatty compound other than the (ii) fatty alcohol(s);
  - wherein said gelling oil phase is present in an amount of from at least about 50% by weight, relative to the weight of the total composition; and
- (b) a lamellar crystalline aqueous gel phase comprising:
  - (i) water and optionally at least one polyol present, wherein the water and optional polyol present in a total amount up to about 50% by weight, relative to the weight of the total composition;
  - (ii) at least one lamellar crystalline phase structurant; and
  - (iii at least one emulsifier.

19. The method of claim 18, wherein the method comprises a step of mechanically shearing the composition prior to applying it to the keratinous substrate.

20. The method of claim 18, wherein the method comprises mechanically shearing the composition while applying it to the keratinous substrate.

* * * * *